US012409331B2

(12) United States Patent
Sullivan et al.

(10) Patent No.: US 12,409,331 B2
(45) Date of Patent: Sep. 9, 2025

(54) WEARABLE CARDIOVERTER DEFIBRILLATOR (WCD) WITH ARTIFICIAL INTELLIGENCE FEATURES

(71) Applicant: WEST AFFUM HOLDINGS DAC, Dublin (IE)

(72) Inventors: Joseph L. Sullivan, Kirkland, WA (US); Zoie R. Engman, Kirkland, WA (US); David P. Finch, Bothell, WA (US); Laura M. Gustavson, Redmond, WA (US); Phillip D. Foshee, Jr., Woodinville, WA (US)

(73) Assignee: WEST AFFUM HOLDINGS DAC, Dublin (IE)

( * ) Notice: Subject to any disclaimer, the term of this patent is extended or adjusted under 35 U.S.C. 154(b) by 590 days.

(21) Appl. No.: 17/669,206

(22) Filed: Feb. 10, 2022

(65) Prior Publication Data

US 2022/0257959 A1 Aug. 18, 2022

Related U.S. Application Data

(60) Provisional application No. 63/149,050, filed on Feb. 12, 2021.

(51) Int. Cl.
*A61N 1/39* (2006.01)
*A61N 1/04* (2006.01)

(52) U.S. Cl.
CPC ........... *A61N 1/3904* (2017.08); *A61N 1/046* (2013.01); *A61N 1/0484* (2013.01); *A61N 1/3925* (2013.01)

(58) Field of Classification Search
CPC .............................. A61N 1/3904; A61N 1/046
(Continued)

(56) References Cited

U.S. PATENT DOCUMENTS 3,724,355 A 4/1973 Busch et al.
3,724,455 A 4/1973 Unger
(Continued)

FOREIGN PATENT DOCUMENTS

CN 111 514 458 A 8/2020
DE 2005060985 A2 6/2007
(Continued)

OTHER PUBLICATIONS

Extended European Search Report received in EP Application No. 22156352.1-1126 dated Jul. 6, 2022; 8 pages total.
(Continued)

*Primary Examiner* — Nicole F Johnson
(74) *Attorney, Agent, or Firm* — POLSINELLI PC

(57) ABSTRACT

Disclosed is a wearable medical device, such as a Wearable Cardioverter Defibrillator, which includes one or more sensors and a processor coupled to the one or more sensors. The processor is configured to record patient-specific information derived from signals output by the one or more sensors while the wearable medical device is being worn and to execute an algorithm to analyze the recorded information, the algorithm being based on data collected from multiple different persons. The processor is further configured to perform an artificial intelligence analysis of the recorded information, to update the algorithm with update information derived from the artificial intelligence analysis of the derived information, and to use the updated algorithm to analyze subsequent signals output by the one or more sensors while the wearable medical is being worn. The disclosed techniques result in a more patient-specific approach, which results in fewer false alarms.

18 Claims, 9 Drawing Sheets

(58) Field of Classification Search
USPC .......................................................... 607/5
See application file for complete search history.

(56) References Cited

U.S. PATENT DOCUMENTS

| | | |
|---|---|---|
| 4,583,524 A | 4/1986 | Hutchins |
| 4,619,265 A | 10/1986 | Morgan et al. |
| 4,666,432 A | 5/1987 | McNeish et al. |
| 4,698,848 A | 10/1987 | Buckley |
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,348,008 A | 9/1994 | Bornn et al. |
| 5,353,793 A | 10/1994 | Bornn |
| RE34,800 E | 11/1994 | Hutchins |
| 5,394,892 A | 3/1995 | Kenny et al. |
| 5,405,362 A | 4/1995 | Kramer et al. |
| 5,429,593 A | 7/1995 | Matory |
| 5,474,574 A | 12/1995 | Payne et al. |
| 5,618,208 A | 4/1997 | Crouse et al. |
| 5,662,690 A | 9/1997 | Cole et al. |
| 5,708,978 A | 1/1998 | Johnsrud |
| 5,741,306 A | 4/1998 | Glegyak et al. |
| 5,782,878 A | 7/1998 | Morgan et al. |
| 5,792,204 A | 8/1998 | Snell |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,280,461 B1 | 8/2001 | Glegyak et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder et al. |
| 6,427,083 B1 | 7/2002 | Owen et al. |
| 6,437,083 B1 | 8/2002 | Brack et al. |
| 6,450,942 B1 | 9/2002 | Lapanashvili et al. |
| 6,529,875 B1 | 3/2003 | Nakajima et al. |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,099,715 B2 | 8/2006 | Korzinov et al. |
| 7,212,850 B2 | 5/2007 | Prystowsky et al. |
| 7,559,902 B2 | 7/2009 | Ting et al. |
| 7,587,237 B2 | 9/2009 | Korzinov et al. |
| 7,753,759 B2 | 7/2010 | Pintor et al. |
| 7,865,238 B2 | 1/2011 | Brink |
| 7,870,761 B2 | 1/2011 | Valentine et al. |
| 7,907,996 B2 | 3/2011 | Prystowsky et al. |
| 7,941,207 B2 | 5/2011 | Korzinov |
| 7,974,689 B2 | 7/2011 | Volpe et al. |
| 8,024,037 B2 | 9/2011 | Kumar |
| 8,135,462 B2 | 3/2012 | Owen et al. |
| 8,140,154 B2 | 3/2012 | Donnelly et al. |
| 8,369,944 B2 | 2/2013 | Macho et al. |
| 8,527,028 B2 | 9/2013 | Kurzweil et al. |
| 8,548,557 B2 | 10/2013 | Garstka et al. |
| 8,560,044 B2 | 10/2013 | Kurzweil et al. |
| 8,615,295 B2 | 12/2013 | Savage et al. |
| 8,644,925 B2 | 2/2014 | Volpe et al. |
| 8,676,313 B2 | 3/2014 | Volpe et al. |
| 8,706,255 B2 | 4/2014 | Phillips et al. |
| 8,742,349 B2 | 6/2014 | Urbon et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,084,583 B2 | 7/2015 | Mazar et al. |
| 9,089,685 B2 | 7/2015 | Sullivan et al. |
| 9,119,547 B2 | 9/2015 | Cazares et al. |
| 9,131,901 B2 | 9/2015 | Volpe et al. |
| 9,132,267 B2 | 9/2015 | Kaib |
| 9,265,432 B2 | 2/2016 | Warren et al. |
| 9,345,898 B2 | 5/2016 | Piha et al. |
| 9,408,548 B2 | 8/2016 | Volpe et al. |
| 9,445,719 B2 | 9/2016 | Libbus et al. |
| 9,454,219 B2 | 9/2016 | Volpe et al. |
| 9,579,020 B2 | 2/2017 | Libbus et al. |
| 9,592,403 B2 | 3/2017 | Sullivan |
| 9,598,799 B2 | 3/2017 | Shoshani et al. |
| 9,675,804 B2 | 6/2017 | Whiting et al. |
| 9,724,008 B2 | 8/2017 | Sullivan et al. |
| 9,757,581 B2 | 9/2017 | Sullivan et al. |
| 9,878,171 B2 | 1/2018 | Kaib |
| 9,895,105 B2 | 2/2018 | Romem |
| 9,901,741 B2 | 2/2018 | Chapman et al. |
| RE46,926 E | 7/2018 | Bly et al. |
| 10,016,613 B2 | 7/2018 | Kavounas |
| 10,076,656 B2 | 9/2018 | Dar et al. |
| 10,192,387 B2 | 1/2019 | Brinig et al. |
| 10,307,133 B2 | 6/2019 | Kaib |
| 10,463,867 B2 | 11/2019 | Kaib et al. |
| 10,589,110 B2 | 3/2020 | Oskin et al. |
| 10,599,814 B2 | 3/2020 | Landrum et al. |
| 11,133,112 B2 | 9/2021 | Teplitzky et al. |
| 11,202,599 B2 | 12/2021 | Saha et al. |
| 11,623,102 B2 | 4/2023 | Schulhauser et al. |
| 2002/0181680 A1 | 12/2002 | Linder et al. |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2006/0173499 A1 | 8/2006 | Hampton et al. |
| 2008/0312709 A1 | 12/2008 | Vollpe et al. |
| 2009/0005827 A1 | 1/2009 | Weintraub et al. |
| 2010/0007413 A1 | 1/2010 | Herleikson |
| 2010/0298899 A1 | 11/2010 | Donnelly et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0191476 A1 | 7/2012 | Reid et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0144355 A1 | 6/2013 | Macho et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0012144 A1 | 1/2014 | Crone |
| 2014/0025131 A1 | 1/2014 | Sullivan et al. |
| 2014/0043149 A1 | 2/2014 | Cowan et al. |
| 2014/0046391 A1 | 2/2014 | Cowan et al. |
| 2014/0070957 A1 | 3/2014 | Longinotti-Buitoni et al. |
| 2014/0163663 A1 | 6/2014 | Poddar et al. |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0161554 A1 | 6/2015 | Sweeney et al. |
| 2015/0297107 A1* | 10/2015 | Sullivan ............... A61N 1/3987 600/523 |
| 2015/0297135 A1 | 10/2015 | Shoshani et al. |
| 2015/0328472 A1 | 11/2015 | Sullivan et al. |
| 2016/0004831 A1 | 1/2016 | Carlson et al. |
| 2016/0076175 A1 | 3/2016 | Rock et al. |
| 2016/0076176 A1 | 3/2016 | Rock et al. |
| 2016/0082277 A1 | 3/2016 | Foshee, Jr. et al. |
| 2016/0113581 A1 | 4/2016 | Amir et al. |

(56) References Cited

U.S. PATENT DOCUMENTS

| | | |
|---|---|---|
| 2016/0135706 A1 | 5/2016 | Sullivan et al. |
| 2016/0256104 A1 | 9/2016 | Romem et al. |
| 2016/0283900 A1 | 9/2016 | Johnson et al. |
| 2016/0303371 A1 | 10/2016 | Whiting et al. |
| 2017/0014073 A1 | 1/2017 | Shoshani et al. |
| 2017/0027469 A1 | 2/2017 | Amir et al. |
| 2017/0036066 A1 | 2/2017 | Chahine |
| 2017/0040758 A1 | 2/2017 | Amir et al. |
| 2017/0056682 A1 | 3/2017 | Kumar et al. |
| 2017/0162840 A1 | 6/2017 | Pendry |
| 2017/0319862 A1 | 11/2017 | Foshee, Jr. et al. |
| 2017/0367591 A1 | 12/2017 | Jorgensen |
| 2018/0116537 A1 | 5/2018 | Sullivan et al. |
| 2018/0117299 A1 | 5/2018 | Gustavson et al. |
| 2018/0184933 A1 | 7/2018 | Sullivan et al. |
| 2018/0185662 A1 | 7/2018 | Foshee, Jr. et al. |
| 2018/0243578 A1 | 8/2018 | Volosin |
| 2018/0348759 A1 | 12/2018 | Freeman et al. |
| 2018/0361165 A1 | 12/2018 | Jaax et al. |
| 2019/0030351 A1 | 1/2019 | Sullivan et al. |
| 2019/0030352 A1 | 1/2019 | Sullivan et al. |
| 2019/0076666 A1 | 3/2019 | Medema |
| 2019/0116896 A1 | 4/2019 | Armour et al. |
| 2019/0321650 A1 | 10/2019 | Raymond et al. |
| 2020/0038671 A1 | 2/2020 | Schulhauser et al. |
| 2020/0398065 A1 | 12/2020 | Engman et al. |

FOREIGN PATENT DOCUMENTS

| | | |
|---|---|---|
| EP | 2305110 A1 | 4/2011 |
| EP | 3 488 771 A1 | 5/2019 |
| JP | 4320257 A | 3/2005 |
| JP | 2010-516431 A | 5/2010 |
| JP | 5963767 A | 1/2014 |
| JP | 2014526282 A | 10/2014 |
| KR | 10-2010-0051777 A | 5/2010 |
| WO | 98/39061 A2 | 9/1998 |
| WO | 2011/146448 A1 | 11/2011 |
| WO | 2012/064604 A1 | 5/2012 |
| WO | 2012/151160 A1 | 11/2012 |
| WO | 2015/056262 A1 | 4/2015 |
| WO | 2020/226904 A1 | 11/2020 |

OTHER PUBLICATIONS

Second Office Action for Japanese Application No. 2022-020005, dated Sep. 26, 2024, 7 pages.

Heartstart MRx and XL AED Algorithm—Application Note, Jul. 2001, Edition 2 Philips Healthcare, USA.

Klein, H. U., Goldenberg, I., and Moss, A. J., "Risk Stratification for Implantable Cardioverter Defibrillator Therapy: The Role of the Wearable Cardioverter-Defibrillator, Clinical update," European Heart Journal, May 31, 2013, pp. 1-14, doi:10.1093/eurheartj/eht167, European Society of Cardiology.

Lifecor LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Pagan-Carlo, et al., "Encircling Overlapping Multipulse Shock Waveforms for Transthoracic Defibrillation," JACC Journals, Dec. 1998, vol. 32 Issue 7, p. 2065-2071.

The LifeVest Network/Patient Data Management System, Zoll, 2015, 2000503 Rev A.

Zoll, LifeVest, Proven protection from Sudden Cardiac Death, issued Mar. 27, 2018, 4 pages. Pittsburgh PA, USA.

International Search Report and Written Opinion for PCT Application No. PCT/US2015/051726, dated May 20, 2016, European Patent Office, Rijswijk, 11 pages.

* cited by examiner

WEARABLE CARDIOVERTER DEFIBRILLATOR (WCD) WITH ARTIFICIAL INTELLIGENCE FEATURES

CROSS REFERENCE TO RELATED APPLICATIONS

This patent application claims the benefit of U.S. Provisional Application No. 63/149,050 filed Feb. 12, 2021, entitled Wearable External Defibrillator, which is expressly incorporated herein by reference in its entirety for all purposes.

This disclosure may be found to be related to U.S. Utility patent application Ser. No. 16/946,512, filed on Jun. 24, 2020, entitled Wearable Cardioverter Defibrillator With AI-Based Features, which is incorporated herein by reference in its entirety for all purposes.

SUMMARY OF THE DISCLOSURE WITH BACKGROUND INFORMATION

When people suffer from some types of heart arrhythmias, the result may be that blood flow to various parts of the body is reduced. Some arrhythmias may even result in a Sudden Cardiac Arrest (SCA). SCA can lead to death very quickly, e.g. within 10 minutes, unless treated in the interim. Some observers have thought that SCA is the same as a heart attack, which it is not.

Some people have an increased risk of SCA. Such people include patients who have had a heart attack, or a prior SCA episode. A frequent recommendation for these people is to receive an Implantable Cardioverter Defibrillator (ICD). The ICD is surgically implanted in the chest, and continuously monitors the patient's electrocardiogram (ECG). If certain types of heart arrhythmias are detected, then the ICD delivers an electric shock through the heart.

As a further precaution, people who have been identified to have an increased risk of an SCA are sometimes provided a Wearable Cardioverter Defibrillator (WCD) system to wear until an ICD is implanted. Early versions of such systems were called wearable cardiac defibrillator systems. A WCD system typically includes a garment, such as a harness, vest, or belt, that the patient wears. The WCD system further includes electronic components, such as a defibrillator and electrodes, coupled with the garment. When the patient wears the WCD system, the electrodes are in electrical contact with the patient's skin, and therefore can help sense the patient's ECG. If a shockable heart arrhythmia (e.g., ventricular fibrillation or VF) is detected from the ECG, the defibrillator delivers an appropriate electric shock through the patient's body, and thus through the heart. The delivered shock may restart the patient's heart and thus save the patient's life.

In accordance with embodiments of the disclosure, a wearable medical device is disclosed which includes one or more sensors and a processor coupled to the one or more sensors. In embodiments, the processor is configured to record patient-specific information derived from signals output by the one or more sensors while the wearable medical device is being worn and execute an algorithm to analyze the recorded information, wherein the algorithm is based at least in part on data collected from multiple different persons. The processor is further configured to perform an artificial intelligence analysis of the recorded information, to update the algorithm with update information derived from the artificial intelligence analysis of the derived information, and to use the updated algorithm to analyze subsequent information derived from signals output by the one or more sensors while the wearable medical is being worn.

None of the subject matter discussed in this section is necessarily prior art and may not be presumed to be prior art simply because it is presented in this section. Plus, any reference to any prior art in this description is not, and should not be taken as, an acknowledgment or any form of suggestion that such prior art forms parts of the common general knowledge in any art in any country. Along these lines, any recognition of problems in the prior art discussed in this section or associated with such subject matter should not be treated as prior art, unless expressly stated to be prior art. Rather, the discussion of any subject matter in this section should be treated as part of the approach taken towards solving the particular problems identified. This approach in and of itself may also be inventive.

BRIEF DESCRIPTION OF THE DRAWINGS

Embodiments of the disclosure are best illustrated by way of example and not by way of limitation in the figures of the accompanying drawings, briefly described below, in which like reference numerals indicate similar elements. It should be noted that references to "an" or "one" embodiment in this disclosure are not necessarily to the same embodiment, and those terms mean at least but not necessarily one.

DETAILED DESCRIPTION OF THE SUBJECT MATTER

In the following detailed description, numerous specific details are set forth. However, it is understood that embodiments of the disclosure may be implemented without these specific details. In some instances, well-known circuits, structures, and techniques have not been shown to avoid obscuring the understanding of this description.

Figure 1:
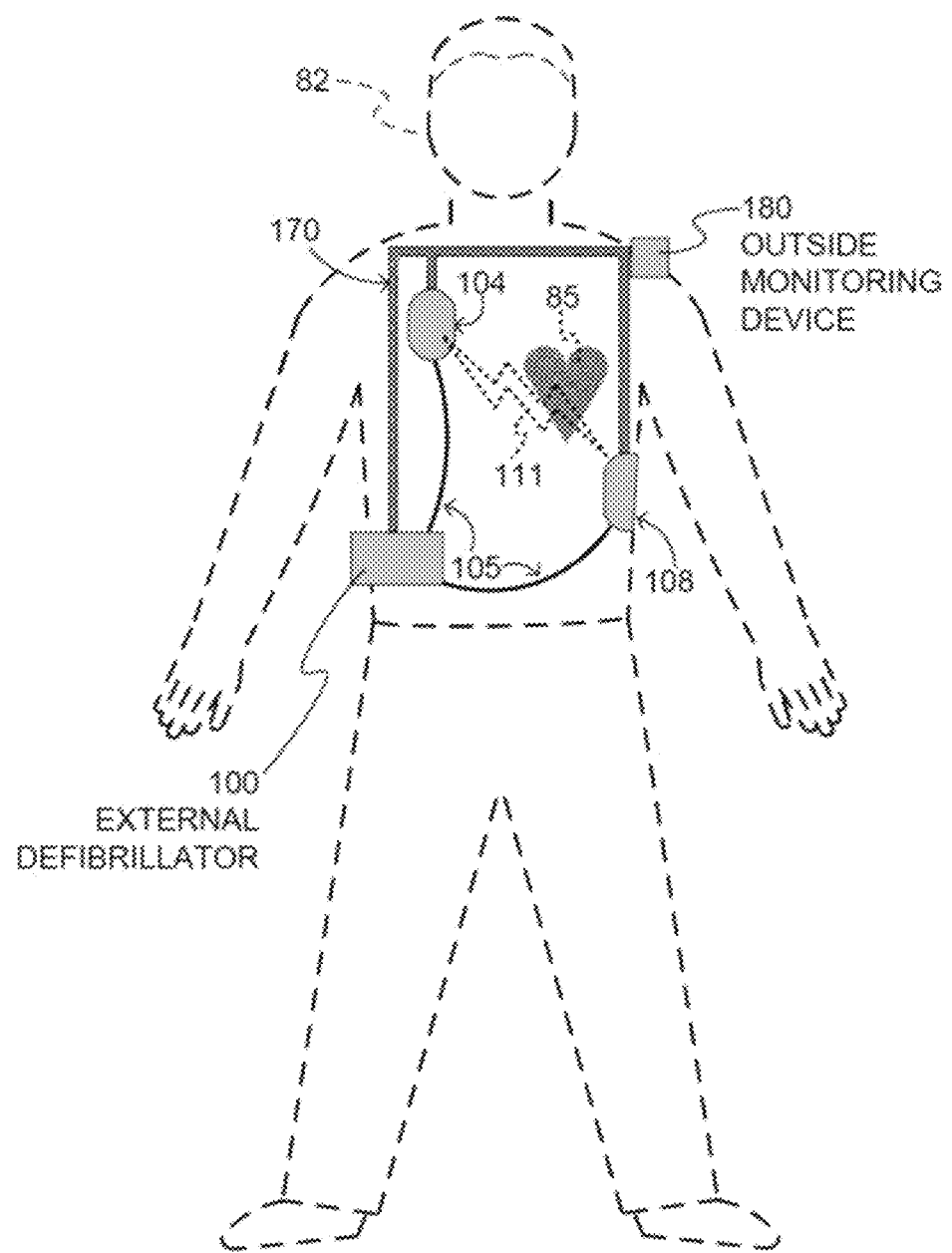
FIG. 1 is a conceptual diagram of a patient wearing an exemplary WCD, made according to embodiments.

FIG. 1 depicts an exemplary WCD system being worn by a patient 82, according to embodiments of the present disclosure. Patient 82 may also be referred to as a person and/or wearer since the patient is wearing components of the WCD system. Patient 82 is ambulatory, which means that, while wearing the wearable portion of the WCD system, patient 82 can walk around and is not necessarily bed ridden. While patient 82 may be considered to be also a "user" of the WCD system, this is not a requirement. For instance, a user of the wearable cardioverter defibrillator (WCD) may also be a clinician such as a doctor, nurse, emergency medical technician (EMT) or other similarly tasked individual or group of individuals. In some cases, a user may even be a bystander. The particular context of these and other related terms within this description should be interpreted accordingly.

A WCD system according to embodiments can be configured to defibrillate the patient who is wearing the designated parts the WCD system. Defibrillating can be by the WCD system delivering an electrical charge to the patient's body in the form of an electric shock. The electric shock can be delivered in one or more pulses.

FIG. 1 also depicts components of a WCD system made according to embodiments. One such component is a support structure 170 that is wearable by ambulatory patient 82. Accordingly, support structure 170 is configured to be worn by ambulatory patient 82 for at least several hours per day, and for at least several days, even a few months. It will be understood that support structure 170 is shown only generically in FIG. 1, and in fact partly conceptually. FIG. 1 is provided merely to illustrate concepts about support structure 170 and is not to be construed as limiting how support structure 170 is implemented, or how it is worn.

Support structure 170 can be implemented in many different ways. For example, it can be implemented in a single component or a combination of multiple components. In embodiments, support structure 170 could include a vest, a half-vest, a garment, etc. In such embodiments such items can be worn similarly to analogous articles of clothing. In embodiments, support structure 170 could include a harness, one or more belts or straps, etc. In such embodiments, such items can be worn by the patient around the torso, hips, over the shoulder, etc. In embodiments, support structure 170 can include a container or housing, which can even be waterproof. In such embodiments, the support structure can be worn by being attached to the patient's body by adhesive material, for example as shown and described in U.S. Pat. No. 8,024,037. Support structure 170 can even be implemented as described for the support structure of US Pat. App. Publication No. US2017/0056682, which is incorporated herein by reference. Of course, in such embodiments, the person skilled in the art will recognize that additional components of the WCD system can be in the housing of a support structure instead of being attached externally to the support structure, for example as described in the US2017/0056682 document. There can be other examples.

The system illustrated in FIG. 1 includes a sample external defibrillator 100. As described in more detail later in this document, some aspects of external defibrillator 100 include a housing and an energy storage module within the housing. As such, in the context of a WCD system, defibrillator 100 is sometimes called a main electronics module. The energy storage module can be configured to store an electrical charge. Other components can cause at least some of the stored electrical charge to be discharged via electrodes through the patient, so as to deliver one or more defibrillation shocks through the patient.

FIG. 1 also illustrates sample defibrillation electrodes 104, 108, which are coupled to external defibrillator 100 via electrode leads 105. Defibrillation electrodes 104, 108 can be configured to be worn by patient 82 in a number of ways. For instance, defibrillator 100 and defibrillation electrodes 104, 108 can be coupled to support structure 170, directly or indirectly. In other words, support structure 170 can be configured to be worn by ambulatory patient 82 so as to maintain at least one of electrodes 104, 108 on the body of ambulatory patient 82, while patient 82 is moving around, etc. The electrode can be thus maintained on the body by being attached to the skin of patient 82, simply pressed against the skin directly or through garments, etc. In some embodiments the electrode is not necessarily pressed against the skin, but becomes biased that way upon sensing a condition that could merit intervention by the WCD system. In addition, many of the components of defibrillator 100 can be considered coupled to support structure 170 directly, or indirectly via at least one of defibrillation electrodes 104, 108.

When defibrillation electrodes 104, 108 make good electrical contact with the body of patient 82, defibrillator 100 can administer, via electrodes 104, 108, a brief, strong electric pulse 111 through the body. Pulse 111 is also known as shock, defibrillation shock, therapy, electrotherapy, therapy shock, etc. Pulse 111 is intended to go through and restart heart 85, in an effort to save the life of patient 82. Pulse 111 can further include one or more pacing pulses of lesser magnitude to simply pace heart 85 if needed, and so on.

A defibrillator typically decides whether to defibrillate or not based on an ECG signal of the patient. However, external defibrillator 100 may initiate defibrillation, or hold-off defibrillation, based on a variety of inputs, with the ECG signal merely being one of these inputs.

A WCD system according to embodiments can obtain data from patient 82. For collecting such data, the WCD system may optionally include at least an outside monitoring device 180. Device 180 is called an "outside" device because it could be provided as a standalone device, for example not within the housing of defibrillator 100. Device 180 can be configured to sense or monitor at least one local parameter. A local parameter can be a parameter of patient 82, or a parameter of the WCD system, or a parameter of the environment, as will be described later in this document.

For some of these parameters, device 180 may include one or more sensors or transducers. Each of such sensors can be configured to sense a parameter of patient 82, and to render an input responsive to the sensed parameter. In some embodiments the input is quantitative, such as values of a sensed parameter; in other embodiments the input is qualitative, such as informing whether or not a threshold is crossed, and so on. Sometimes these inputs about patient 82 are also referred to herein as physiological inputs and patient inputs. In embodiments, a sensor can be construed more broadly, as encompassing many individual sensors.

Optionally, device 180 is physically coupled to support structure 170. In addition, device 180 may be in operative communication with other components that are coupled to support structure 170. Such communication can be implemented by a communication module, as will be deemed applicable by a person skilled in the art in view of this description.

In embodiments, one or more of the components of the shown WCD system may be customized for patient 82. This customization may include a number of aspects. For instance, support structure 170 can be fitted to the body of patient 82. For another instance, baseline physiological parameters of patient 82 can be measured, such as the heart rate of patient 82 while resting, while walking, motion detector outputs while walking, etc. The measured values of such baseline physiological parameters can be used to customize the WCD system, in order to make its diagnoses more accurate, since patients' bodies differ from one another. Of course, such parameter values can be stored in a memory of the WCD system, and so on. Moreover, a programming interface can be made according to embodiments, which receives such measured values of baseline physiological parameters. Such a programming interface may input automatically in the WCD system these, along with other data.

Figure 2:
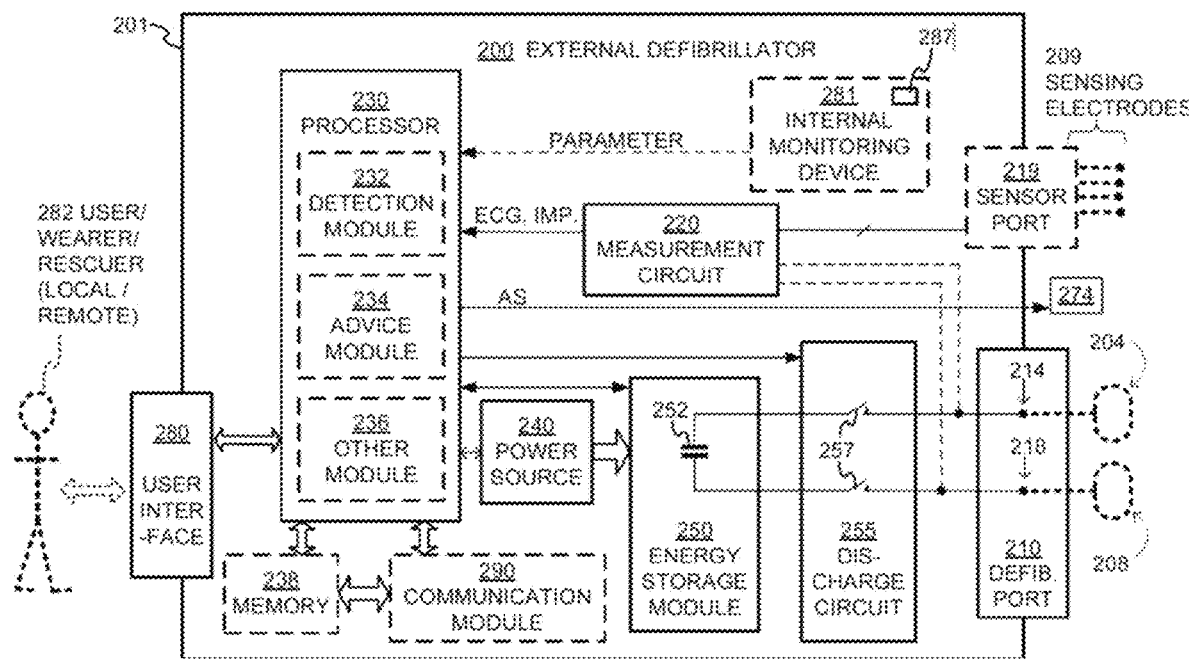
FIG. 2 is a diagram showing sample components of an external defibrillator, made according to embodiments.

FIG. 2 is a diagram showing components of an external defibrillator 200, made according to embodiments. These components can be, for example, included in external defibrillator 100 of FIG. 1. The components shown in FIG. 2 can be provided in a housing 201, which may also be referred to as casing 201.

External defibrillator 200 is intended for a patient who would be wearing it, such as ambulatory patient 82 of FIG. 1. Defibrillator 200 may further include a user interface 280 for a user 282. User 282 can be patient 82, also known as wearer 82. Or, user 282 can be a local rescuer at the scene, such as a bystander who might offer assistance, or a trained person. Or, user 282 might be a remotely located trained caregiver in communication with the WCD system.

User interface 280 can be made in a number of ways. User interface 280 may include output devices, which can be visual, audible, or tactile, for communicating to a user by outputting images, sounds or vibrations. Images, sounds, vibrations, and anything that can be perceived by user 282 can also be called human-perceptible indications (HPIs). There are many examples of output devices. For example, an output device can be a light, or a screen to display what is sensed, detected and/or measured, and provide visual feedback to rescuer 282 for their resuscitation attempts, and so on. Another output device can be a speaker, which can be configured to issue voice prompts, beeps, loud alarm sounds and/or words to warn bystanders, etc.

User interface 280 may further include input devices for receiving inputs from users. Such input devices may include various controls, such as push buttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock.

Defibrillator 200 may include an internal monitoring device 281. Device 281 is called an "internal" device because it is incorporated within housing 201. Monitoring device 281 can sense or monitor patient parameters such as patient physiological parameters, system parameters and/or environmental parameters, all of which can be called patient data. In other words, internal monitoring device 281 can be complementary or an alternative to outside monitoring device 180 of FIG. 1. Allocating which of the parameters are to be monitored by which of monitoring devices 180, 281 can be done according to design considerations. Device 281 may include one or more sensors, as also described elsewhere in this document.

Patient parameters may include patient physiological parameters. Patient physiological parameters may include, for example and without limitation, those physiological parameters that can be of any help in detecting whether or not the patient is in need of a shock or other intervention or assistance. Patient physiological parameters may also optionally include the patient's medical history, event history and so on. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, monitoring devices 180, 281 may include one or more sensors configured to acquire patient physiological signals. Examples of such sensors or transducers include one or more electrodes to detect ECG data, a perfusion sensor, a pulse oximeter, a device for detecting blood flow (e.g. a Doppler device), a sensor for detecting blood pressure (e.g. a cuff), an optical sensor, illumination detectors and sensors perhaps working together with light sources for detecting color change in tissue, a motion sensor, a device that can detect heart wall movement, a sound sensor, a device with a microphone, an SpO2 sensor, and so on. In view of this disclosure, it will be appreciated that such sensors can help detect the patient's pulse, and can therefore also be called pulse detection sensors, pulse sensors, and pulse rate sensors. In addition, a person skilled in the art may implement other ways of performing pulse detection.

In some embodiments, a local parameter is a trend that can be detected in a monitored physiological parameter of patient 282. A trend can be detected by comparing values of parameters at different times over short and long terms. Parameters whose detected trends can particularly help a cardiac rehabilitation program include: (a) cardiac function (e.g. ejection fraction, stroke volume, cardiac output, etc.); (b) heart rate variability at rest or during exercise; (c) heart rate profile during exercise and measurement of activity vigor, such as from the profile of an accelerometer signal and informed from adaptive rate pacemaker technology; (d) heart rate trending; (e) perfusion, such as from SpO2, CO2, or other parameters such as those mentioned above, (f) respiratory function, respiratory rate, etc.; (g) motion, level of activity; and so on. Once a trend is detected, it can be stored and/or reported via a communication link, along perhaps with a warning if warranted. From the report, a physician monitoring the progress of patient 282 will know about a condition that is either not improving or deteriorating.

Patient state parameters may include recorded aspects of patient 282, such as motion, posture, whether the patient has spoken recently and maybe also what the patient said, and so on, plus optionally the history of these parameters. Or, one of these monitoring devices could include a location sensor such as a Global Positioning System (GPS) location sensor. Such a sensor can detect the location, plus a speed can be determined as a rate of change of location over time. Many motion detectors output a motion signal that is indicative of the motion of the detector, and thus of the patient's body. Patient state parameters can be very helpful in narrowing down the determination of whether SCA is indeed taking place.

A WCD system made according to embodiments may thus include a motion detector. In embodiments, a motion detector can be implemented within monitoring device 180 or monitoring device 281. Such a motion detector can be made in many ways as is known in the art, for example by using an accelerometer. In this example, a motion detector 287 is implemented within monitoring device 281. A motion detector of a WCD system according to embodiments can be configured to detect a motion event. A motion event can be defined as is convenient, for example a change in motion from a baseline motion or rest, etc. In such cases, a sensed patient parameter is motion.

System parameters of a WCD system can include system identification, battery status, system date and time, reports of self-testing, records of data entered, records of episodes and intervention, and so on. In response to the detected motion event, the motion detector may render or generate, from the detected motion event or motion, a motion detection input that can be received by a subsequent device or functionality.

Environmental parameters can include ambient temperature and pressure. Moreover, a humidity sensor may provide information as to whether or not it is likely raining. Presumed patient location could also be considered an environmental parameter. The patient location could be presumed, if monitoring device 180 or 281 includes a GPS location sensor as per the above, and if it is presumed that the patient is wearing the WCD system.

Defibrillator 200 typically includes a defibrillation port 210, which can be a socket in housing 201. Defibrillation port 210 includes electrical nodes 214, 218. Leads of defibrillation electrodes 204, 208, such as leads 105 of FIG. 1, can be plugged into defibrillation port 210, so as to make electrical contact with nodes 214, 218, respectively. It is also possible that defibrillation electrodes 204, 208 are connected continuously to defibrillation port 210, instead. Either way, defibrillation port 210 can be used for guiding, via electrodes, to the wearer at least some of the electrical charge that has been stored in an energy storage module 250 that is described more fully later in this document. The electric charge will be the shock for defibrillation, pacing, and so on.

Defibrillator 200 may optionally also have a sensor port 219 in housing 201, which is also sometimes known as an ECG port. Sensor port 219 can be adapted for plugging in sensing electrodes 209, which are also known as ECG electrodes and ECG leads. It is also possible that sensing electrodes 209 can be connected continuously to sensor port 219, instead. Sensing electrodes 209 are types of transducers that can help sense an ECG signal, e.g. a 12-lead signal, or a signal from a different number of leads, especially if they make good electrical contact with the body of the patient and in particular with the skin of the patient. As with defibrillation electrodes 204, 208, the support structure can be configured to be worn by patient 282 so as to maintain sensing electrodes 209 on a body of patient 282. For example, sensing electrodes 209 can be attached to the inside of support structure 170 for making good electrical contact with the patient, similarly with defibrillation electrodes 204, 208.

Optionally a WCD system according to embodiments also includes a fluid that it can deploy automatically between the electrodes and the patient's skin. The fluid can be conductive, such as by including an electrolyte, for establishing a better electrical contact between the electrodes and the skin. Electrically speaking, when the fluid is deployed, the electrical impedance between each electrode and the skin is reduced. Mechanically speaking, the fluid may be in the form of a low-viscosity gel, so that it does not flow away, after being deployed, from the location it is released near the electrode. The fluid can be used for both defibrillation electrodes 204, 208, and for sensing electrodes 209.

The fluid may be initially stored in a fluid reservoir, not shown in FIG. 2. Such a fluid reservoir can be coupled to the support structure. In addition, a WCD system according to embodiments further includes a fluid deploying mechanism 274. Fluid deploying mechanism 274 can be configured to cause at least some of the fluid to be released from the reservoir and be deployed near one or both of the patient locations to which electrodes 204, 208 are configured to be attached to the patient. In some embodiments, fluid deploying mechanism 274 is activated prior to the electrical discharge responsive to receiving activation signal AS from a processor 230, which is described more fully later in this document.

In some embodiments, defibrillator 200 also includes a measurement circuit 220, as one or more of its working together with its sensors or transducers. Measurement circuit 220 senses one or more electrical physiological signals of the patient from sensor port 219, if provided. Even if defibrillator 200 lacks sensor port 219, measurement circuit 220 may optionally obtain physiological signals through nodes 214, 218 instead, when defibrillation electrodes 204, 208 are attached to the patient. In these cases, the input reflects an ECG measurement. The patient parameter can be an ECG, which can be sensed as a voltage difference between electrodes 204, 208. In addition, the patient parameter can be an impedance, which can be sensed between electrodes 204, 208 and/or between the connections of sensor port 219 considered pairwise. Sensing the impedance can be useful for detecting, among other things, whether these electrodes 204, 208 and/or sensing electrodes 209 are not making good electrical contact with the patient's body. These patient physiological signals may be sensed when available. Measurement circuit 220 can then render or generate information about them as inputs, data, other signals, etc. As such, measurement circuit 220 can be configured to render a patient input responsive to a patient parameter sensed by a sensor. In some embodiments, measurement circuit 220 can be configured to render a patient input, such as values of an ECG signal, responsive to the ECG signal sensed by sensing electrodes 209. More strictly speaking, the information rendered by measurement circuit 220 is output from it, but this information can be called an input because it is received as an input by a subsequent device or functionality.

Defibrillator 200 also includes a processor 230. Processor 230 may be implemented in a number of ways in various embodiments. Such ways include, by way of example and not of limitation, digital and/or analog processors such as microprocessors and Digital Signal Processors (DSPs), controllers such as microcontrollers, software running in a machine, programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 230 may include, or have access to, a non-transitory storage medium, such as memory 238 that is described more fully later in this document. Such a memory can have a nonvolatile component for storage of machine-readable and machine-executable instructions. A set of such instructions can also be called a program. The instructions, which may also be referred to as "software," generally provide functionality by performing acts, operations and/or methods as may be disclosed herein or understood by one skilled in the art in view of the disclosed embodiments. In some embodiments, and as a matter of convention used herein, instances of the software may be referred to as a "module" and by other similar terms. Generally, a module includes a set of the instructions so as to offer or fulfill a particular functionality. Embodiments of modules and the functionality delivered are not limited by the embodiments described in this document.

Processor 230 can be considered to have a number of modules. One such module can be a detection module 232. Detection module 232 can include a Ventricular Fibrillation (VF) detector. The patient's sensed ECG from measurement circuit 220, which can be available as inputs, data that reflect values, or values of other signals, may be used by the VF detector to determine whether the patient is experiencing VF. Detecting VF is useful because VF typically results in SCA. Detection module 232 can also include a Ventricular Tachycardia (VT) detector, and so on.

Another such module in processor 230 can be an advice module 234, which generates advice for what to do. The advice can be based on outputs of detection module 232. There can be many types of advice according to embodiments. In some embodiments, the advice is a shock/no shock determination that processor 230 can make, for example via advice module 234. The shock/no shock determination can be made by executing a stored Shock Advisory Algorithm. A Shock Advisory Algorithm can make a shock/no shock determination from one or more ECG signals that are captured according to embodiments and determine whether or not a shock criterion is met. The determination can be made from a rhythm analysis of the captured ECG signal or otherwise.

In some embodiments, when the determination is to shock, an electrical charge is delivered to the patient. Delivering the electrical charge is also known as discharging and shocking the patient. As mentioned above, such can be for defibrillation, pacing, and so on.

In ideal conditions, a very reliable shock/no shock determination can be made from a segment of the sensed ECG signal of the patient. In practice, however, the ECG signal is often corrupted by electrical noise, which makes it difficult to analyze. Too much noise sometimes causes an incorrect detection of a heart arrhythmia, resulting in a false alarm to the patient. Noisy ECG signals may be handled as described in U.S. patent application Ser. No. 16/037,990, filed on Jul. 17, 2018 and since published as US 2019/0030351 A1, and also in U.S. patent application Ser. No. 16/038,007, filed on Jul. 17, 2018 and since published as U.S. Patent Publication No. 2019/0030352 A1, both by the same applicant and incorporated herein by reference.

Processor 230 can include additional modules, such as other module 236, for other functions. In addition, if internal monitoring device 281 is indeed provided, processor 230 may receive its inputs, etc.

Defibrillator 200 optionally further includes a memory 238, which can work together with processor 230. Memory 238 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 238 is thus a non-transitory storage medium. Memory 238, if provided, can include programs for processor 230, which processor 230 may be able to read and execute. More particularly, the programs can include sets of instructions in the form of code, which processor 230 may be able to execute upon reading. The programs may also include other information such as configuration data, profiles, scheduling etc. that can be acted on by the instructions. Executing is performed by physical manipulations of physical quantities, and may result in functions, operations, processes, acts, actions and/or methods to be performed, and/or the processor to cause other devices or components or blocks to perform such functions, operations, processes, acts, actions and/or methods. The programs can be operational for the inherent needs of processor 230, and can also include protocols and ways that decisions can be made by advice module 234. In addition, memory 238 can store prompts for user 282 if this user is a local rescuer. Moreover, memory 238 can store data. This data can include patient data, system data and environmental data, for example as learned by internal monitoring device 281 and outside monitoring device 180. The data can be stored in memory 238 before it is transmitted out of defibrillator 200, or be stored there after it is received by defibrillator 200.

Defibrillator 200 can optionally include a communication module 290, for establishing one or more wired or wireless communication links with other devices of other entities, such as a remote assistance center, Emergency Medical Services (EMS), and so on. The communication links can be used to transfer data and commands. The data may be patient data, event information, therapy attempted, CPR performance, system data, environmental data, and so on. For example, communication module 290 may transmit wirelessly, e.g., on a daily basis, heart rate, respiratory rate, and other vital signs data to a server accessible over the internet, for instance as described in US Pat. Publ'n 20140043149. This data can be analyzed directly by the patient's physician and can also be analyzed automatically by algorithms designed to detect a developing illness and then notify medical personnel via text, email, phone, etc. Module 290 may also include such interconnected sub-components as may be deemed necessary by a person skilled in the art, for example an antenna, portions of a processor, supporting electronics, outlet for a telephone or a network cable, etc.

Defibrillator 200 may also include a power source 240. To enable portability of defibrillator 200, power source 240 typically includes a battery. Such a battery is typically implemented as a battery pack, which can be rechargeable or not. Sometimes a combination is used of rechargeable and non-rechargeable battery packs. Other embodiments of power source 240 can include an AC power override, for where AC power will be available, an energy-storing capacitor, and so on. Appropriate components may be included to provide for charging or replacing power source 240. In some embodiments, power source 240 is controlled and/or monitored by processor 230.

Defibrillator 200 may additionally include an energy storage module 250. Energy storage module 250 can be coupled to the support structure of the WCD system, for example either directly or via the electrodes and their leads. Module 250 is where some electrical energy can be stored temporarily in the form of an electrical charge, when preparing it for discharge to administer a shock. In embodiments, module 250 can be charged from power source 240 to the desired amount of energy, as controlled by processor 230. In typical implementations, module 250 includes a capacitor 252, which can be a single capacitor or a system of capacitors, and so on. In some embodiments, energy storage module 250 includes a device that exhibits high power density, such as an ultracapacitor. As described above, capacitor 252 can store the energy in the form of an electrical charge, for delivering to the patient.

A decision to shock can be made responsive to the shock criterion being met, as described below. When the decision is to shock, processor 230 can be configured to cause at least some or all of the electrical charge stored in module 250 to be discharged through patient 82 while the support structure is worn by patient 82, so as to deliver a shock 111 to patient 82.

For causing the discharge, defibrillator 200 moreover includes a discharge circuit 255. When the decision is to shock, processor 230 can be configured to control discharge circuit 255 to discharge the patient at least some of all of the electrical charge stored in energy storage module 250. Discharging can be to nodes 214, 218, and from there to defibrillation electrodes 204, 208, so as to cause a shock to be delivered to the patient. Circuit 255 can include one or more switches 257. Switches 257 can be made in a number of ways, such as by an H-bridge, and so on. Circuit 255 could also be thus controlled via processor 230, and/or user interface 280.

A time waveform of the discharge may be controlled by thus controlling discharge circuit 255. The amount of energy of the discharge can be controlled by how much energy storage module has been charged, and also by how long discharge circuit 255 is controlled to remain open. Defibrillator 200 can optionally include other components.

Figure 3:
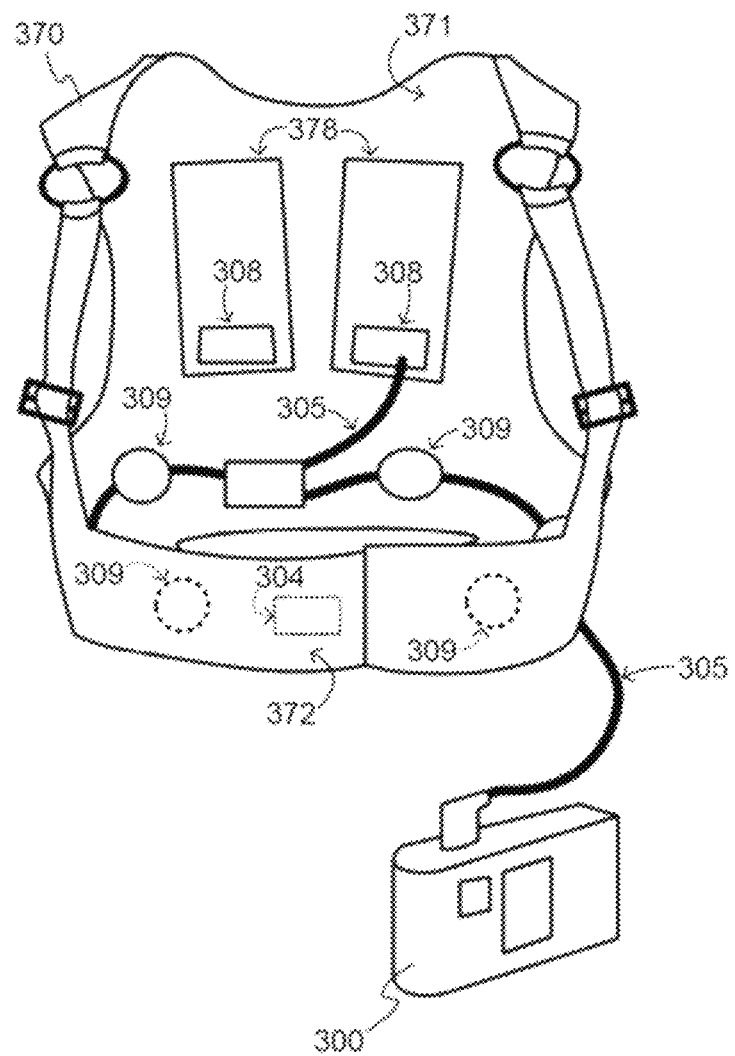
FIG. 3 is a diagram of sample embodiments of components of a WCD system made in accordance with this disclosure.

FIG. 3 is a diagram of sample embodiments of components of an exemplary WCD system. In this particular example, a support structure 370 includes a vest-like wearable garment. Support structure 370 has a back side 371 and a front side 372 that closes in front of the chest of the patient.

The WCD system of FIG. 3 also includes an external defibrillator 300. FIG. 3 does not show any support for external defibrillator 300, which may be carried in a purse, on a belt, by a strap over the shoulder, and so on. Wires 305 connect external defibrillator 300 to electrodes 304, 308, 309. Of those, electrodes 304, 308 are defibrillation electrodes, and electrodes 309 are ECG sensing electrodes.

Support structure 370 is configured to be worn by the ambulatory patient so as to maintain electrodes 304, 308, 309 on a body of the patient. Indeed, back defibrillation electrodes 308 are maintained in pockets 378. Of course, the inside of pockets 378 can be made with loose netting, so that electrodes 308 can contact the back of the patient, especially with the help of the conductive fluid that has been deployed. In addition, sensing electrodes 309 are maintained in positions that surround the patient's torso, for sensing ECG signals and/or the impedance of the patient.

ECG signals in a WCD system may include too much electrical noise to be useful. To ameliorate the problem, multiple ECG sensing electrodes 309 are provided, for presenting many options to processor 230. These options are different vectors for sensing the ECG signal, as described now in more detail.

Figure 4:
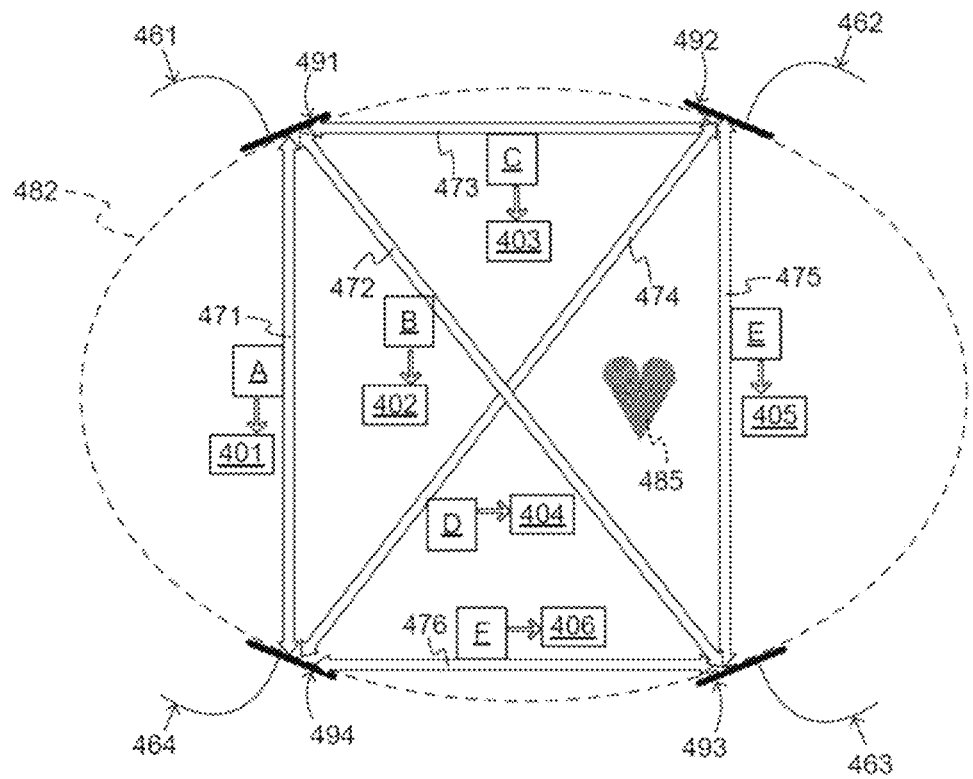
FIG. 4 is a conceptual diagram for illustrating how multiple electrodes of a WCD system may be used for sensing ECG signals along different vectors according to embodiments.

FIG. 4 is a conceptual diagram illustrating how multiple electrodes of a WCD system may be used for sensing ECG signals along different vectors according to embodiments. In FIG. 4, the sizes/shapes/positions of the torso, electrodes and heart are approximate and not to scale. A section of a patient 482 having a heart 485 is shown. In FIG. 4, patient 482 is viewed from the top, patient 482 is facing downwards, and the plane of FIG. 4 intersects patient 482 at the torso of the patient.

Four ECG sensing electrodes 491, 492, 493, 494 are maintained on the torso of patient 482, and have respective wire leads 461, 462, 463, 464. It will be recognized that electrodes 491, 492, 493, 494 surround the torso, similarly with sensing electrodes 309 in the example of FIG. 3.

Any pair of these four ECG sensing electrodes 491, 492, 493, 494 defines a vector, along which an ECG signal may be sensed and/or measured. As such, electrodes 491, 492, 493, 494 define six vectors 471, 472, 473, 474, 475, 476. FIG. 4 thus illustrates a multi-vector embodiment.

These vectors 471, 472, 473, 474, 475, 476 define channels A, B, C, D, E, F respectively. ECG signals 401, 402, 403, 404, 405, 406 may thus be sensed and/or measured from channels A, B, C, D, E, F, respectively, and in particular from the appropriate pairings of wire leads 461, 462, 463, 464 for each channel.

In FIG. 4 it will be understood that electrodes 491, 492, 493, 494 are drawn as being on the same plane for simplicity and as is preferred, while that may not necessarily be the case. Accordingly, vectors 471, 472, 473, 474, 475, 476 are not necessarily on the same plane, either.

In embodiments, in order to more correctly make the shock/no-shock determination, a WCD may assess which of ECG signals 401, 402, 403, 404, 405, 406 is best for rhythm analysis and interpretation. For example, ECG signals that have the most noise may be ignored, discarded, not considered, while leaving the remaining ECG signals as candidates for making the shock/no shock determination.

In other embodiments, the vectors may be aggregated to determine the patient's heart rate and/or RR intervals. For example, in some embodiments the aggregation can be implemented as disclosed in U.S. Pat. No. 9,757,581 issued Sep. 12, 2017 entitled "Wearable Cardioverter Defibrillator Components Making Aggregate Shock/No Shock Determination From Two Or More ECG Signals," which is incorporated herein by reference for all purposes.

Because a WCD is worn by ambulatory patients, patient movement may cause changes at the electrode-skin interface, resulting in noise on an ECG signal. This noise can be a significant problem by interfering with ECG interpretation.

In embodiments, the WCD device uses four monitoring electrodes which can generate six differential ECG vectors. When the patient wearing the WCE is moving, some ECG electrodes may move more than others, resulting in some ECG vectors having more noise than other ECG vectors. In embodiments, different assessment methods are used on all of ECG vectors. If the assessments for an ECG vector have similar results, then the ECG vector is deemed reliable. The ECG vectors deemed to be reliable can then be used in a rhythm analysis, resulting in a more accurate result.

In some embodiments in which only a single ECG vector is used, different assessment methods can be used on the single vector, with only portions of the ECG signal that are deemed reliable being used in the rhythm analysis. In an enhancement, the WCD device can be configured to prompt the patient to reduce activity if the number of ECG portions that are deemed unreliable exceeds a threshold. This can reduce the amount of noise generated by the patient's movement and increase the number of ECG portions that are deemed reliable.

Threshold-Based Shock Analysis

Generally stated, WCDs implement an algorithm for analyzing patient parameters when deciding when to shock a patient. For instance, defibrillator algorithms may use a patient's heart rate in combination with a supraventricular tachycardia (SVT) discriminator (such as QRS width or morphology) to decide when to shock, but the personalization of the algorithm can be limited. Heart rate thresholds and device response times may be adjusted, but otherwise the algorithm typically uses parameters that are largely fixed and relatively the same for each patient. Although threshold-based shock analysis embodiments may perform well, the present disclosure describes embodiments of a WCD system configured to dynamically adjust a shock decision algorithm based on patient parameters of the wearer to reduce unnecessary alarms, alerts, and episodes.

Regression-Based Shock Analysis

In accordance with one embodiment of the disclosure, making a shock decision may be accomplished by computing a shock decision index that is based on measured values of patient parameters, then basing a shock decision on the value of the shock index. For example, a "Shock Index" may be computed using the following formula:

$$\text{Shock Index} = A*\text{Heart Rate}^2 + B*\text{Heart Rate} + C*\text{Width}^2 + D*\text{Width} + E$$

In that equation, the Heart Rate corresponds to the wearing patient's heart rate, and the Width corresponds to the QRS width of the wearing patient's ECG. In addition, the variables A, B, C, D, and E are "weighting variables" (also referred to as coefficients) used to fine tune, or slightly affect the importance of, each individual component of the formula. Each of those coefficients may be derived using a "classification algorithm" applied to a large database of shockable and non-shockable signals. In other words, the classification algorithm may perform machine learning techniques to evaluate a database of recorded patient parameters which are known to represent either shockable or non-shockable events. In this way, the classification algorithm may iterate over that database of known-good event data to achieve coefficients that result in a computed Shock Index that achieves the highest (within practical determination) probability of accurately representing a likelihood that a patient is experiencing a shockable event.

The example formula shown includes squared values for both parameters. Other formulas may not include the squared values for one or both parameters. Other formulas may include parameters to other powers, such as the third or fourth power, or may include nonlinear operations such as logarithms or exponentiation. One skilled in the art will realize that a logistic regression formula is but one example of a machine learning technique that relates linear inputs to a binary output.

It should be noted that the Shock Index formula described above produces a range of values in integer or decimal format. However, alternative embodiments that implement other machine learning techniques may result in a binary answer (i.e., a direct "shockable" or "non-shockable" result). These and other implementations will become apparent from a review of this disclosure.

Generally stated, various embodiments of the classification algorithm may be implemented using a logistic regression, a support vector machine, a convolutional neural network, a recurrent neural network, a naïve bayes classifier, k-nearest neighbors, a decision tree, or other similar technique. "Ensemble" techniques may also be employed that use methods such as "bagging," boosting, stacking, or averaging of multiple outputs. Implementations of the these and/or other artificial intelligence techniques are often referred to as "machine learning."

Figure 5:
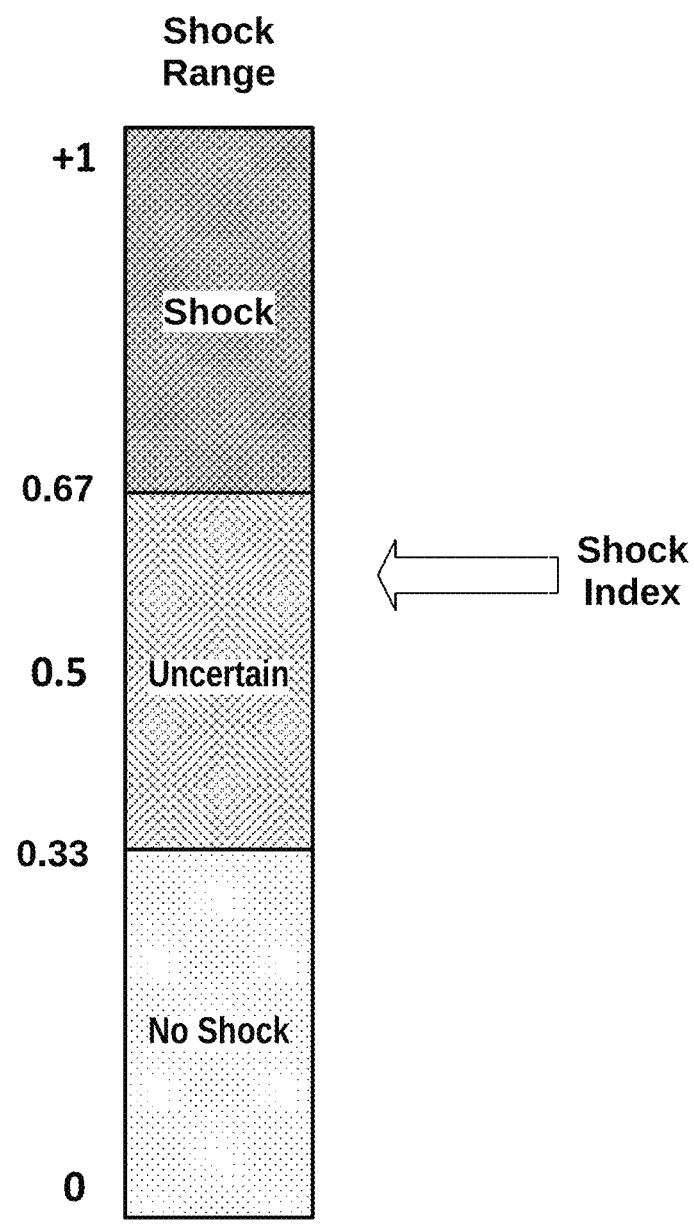
FIG. 5 is a conceptual diagram generally illustrating a shock range of values that generally indicate whether a patient is experiencing a shockable event.

Referring briefly to FIG. 5, a Shock Index computed using the formula above would be compared to a "Shock Range" to determine whether to shock. In this particular embodiment, the Shock Range may be between zero (0) and one (1) and represent a continuum of likelihoods that the sensed patient parameters represent a shockable event. In this particular example, a Shock Index of 0.5 could be used as a simple shock/no-chock determining threshold. Alternatively, a Shock Index between zero and 0.33 could indicate that a shock is unnecessary; a Shock Index between 0.67 and 1 could indicate that a shock is necessary; and a Shock Index between 0.33 and 0.67 could indicate that it is uncertain whether a shock in necessary. In such an approach, Shock Index values in the uncertain range might be handled in various ways, such as by issuing a shock alert but providing a patient with more time to respond to the alert, or additional prompts may be provided to the patient.

One advantage of this method is that it provides better separation between shockable and non-shockable segments than either parameter would have alone. In other words, this approach has a lower probability of giving an inappropriate shock while maintaining the highest sensitivity.

Again, in implementations where a shock decision formula is used that returns a binary result, the Shock Range might simply represent a binary decision point. A shock decision formula of zero, for example, may indicate that a shock is not currently advised. A shock decision formula of one, for example, may indicate that a shock is currently deemed necessary. Still other alternative implementations are possible.

Figure 6:
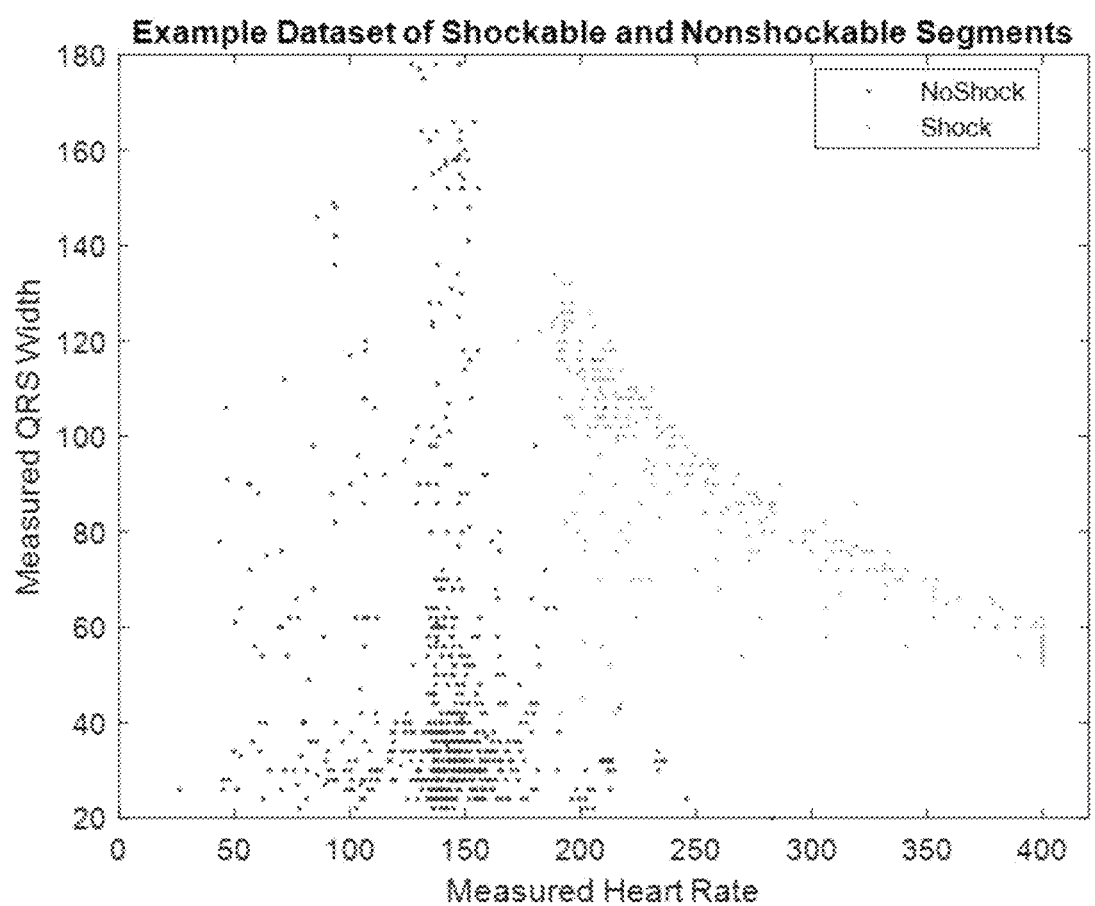
FIG. 6 is a scattergram that represents a dataset of 1592 ECG segments that have been annotated as either shockable or non-shockable.

One specific example will now be used to illustrate the effectiveness of the approach described above. Referring to FIG. 6, a scattergram 601 is displayed that represents a dataset of 1592 ECG segments that have been annotated as either shockable or non-shockable. The scattergram 601 represents real-world data accumulated from numerous patients over time. Dots plotted in red represent non-shockable ECG segments, and dots plotted in blue represent shockable ECG segments.

In accordance with embodiments of the disclosure, a logistic regression method is used to calculate coefficients (or weighting variables) in the formula listed above. The product of that logistic regression method is the following Shock Index formula:

$$\text{Shock Index} = -0.0005*HR^2 + 0.33*HR - 0.0014*\text{Width}^2 + 0.32*\text{Width} - 59.64$$

Figure 7A:
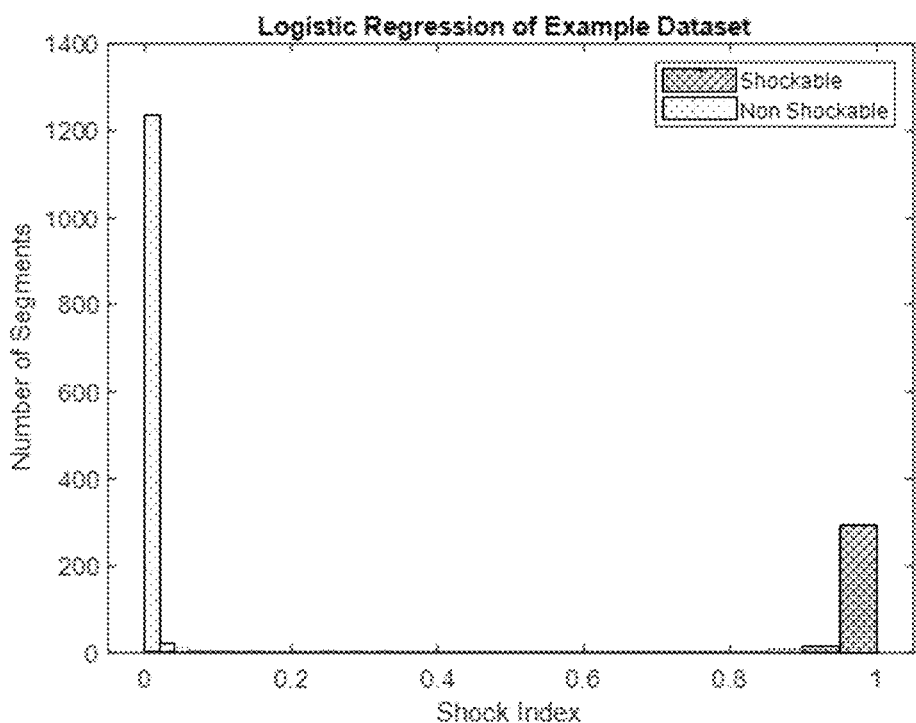
FIGS. 7A and 7B are a histogram, at different zoom levels, that illustrates Shock Indices computed using a Shock Index formula with coefficients computed using a logistic regression method, in accordance with embodiments of the disclosure.
Figure 7B:
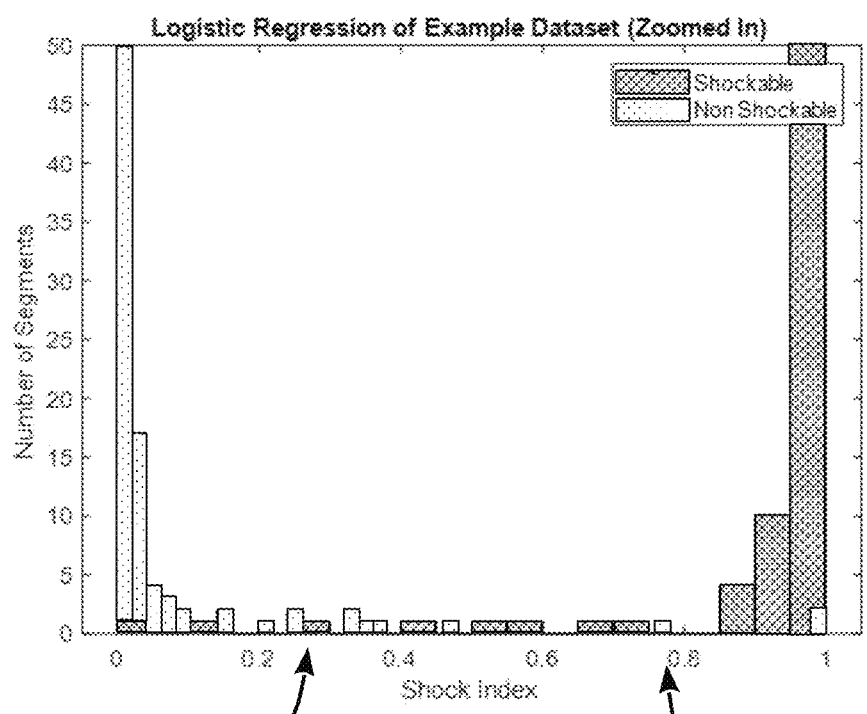

Again, in the foregoing formula, HR corresponds to heart rate and Width corresponds to QRS width. Referring now to FIGS. 7A and 7B, a histogram illustrates Shock Indices that were computed using this Shock Index formula with the coefficients computed using the logistic regression method just described. This approach distinguished shockable from non-shockable segments. Using a single shock index threshold of 0.5 (see, e.g., FIG. 5) results in only two false positive shock decisions (702) and four false negative shock decisions (705).

In this example embodiment, heart rate and QRS width are used as the measured patient parameters. However, in other embodiments, many other features can be measured and included. Examples include, but are not limited to, heart rate stability, the rate of change of the heart rate, consistency of the QRS width, similarity of morphology to a stored template, QRS organization, percentage of time spent near the baseline, frequency content, and other parameters. In other embodiments, parameters could also be extracted from an accelerometer signal, from a respiration signal, a pulse oximeter signal, spoken or ambient audio inputs, or other device. The duration of signals may also be a factor. Multiple parameters can be included into a "Shock Index" formula, and optimal parameters calculated for each.

Further embodiments may include methods for distinguishing VT from slow VF. This could be done based on the heart rate alone (e.g., using a VF threshold 200 BPM), or it could consider factors such as the QRS Organization as described in U.S. patent application Ser. No. 16/554,410 filed Aug. 28, 2019 entitled "Methods and Systems for Distinguishing VT from VF". Bradycardia and asystole could also be identified based on heart rate.

The foregoing discussion sets forth embodiments that make use of artificial intelligence to develop an improved algorithm for computing a shock index that can be used in making shock/no-shock determinations. What follows are additional embodiments that make use of artificial intelligence to further improve a shock/no-shock determination algorithm.

Personalized Classification Algorithms

In one implementation, a set of shockable and non-shockable ECG segments are collected and a classification algorithm, such as described above, may be used to calculate the proper coefficients. Such an approach can work well for most people, but it does not tailor the algorithm for an individual patient. To achieve better performance for each patient, embodiments of the present disclosure, as shown in FIG. 8, include a wearable device configured to collect signals from a given patient, add the signals to a patient specific database to form a new dataset, and then re-calculate coefficients using the new dataset.

Figure 8:
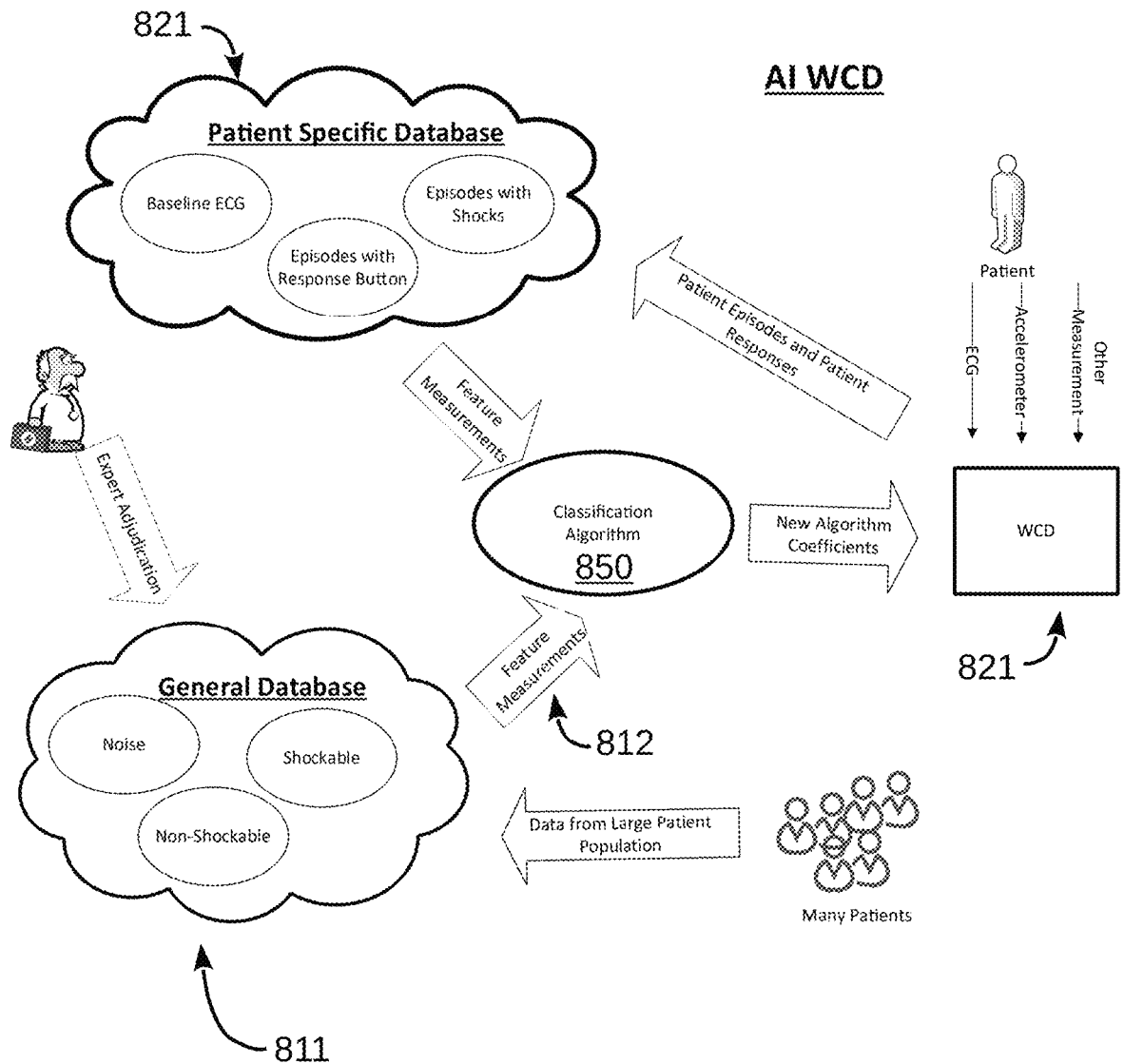
FIG. 8 is a conceptual diagram of a WCD environment in which a medical device, configured in accordance with the teachings of this disclosure, is used to evaluate patient-specific data based on artificial intelligence methods, in accordance with embodiments of the disclosure.

By way of overview, and as illustrated in FIG. 8, a WCD environment 800 includes at least a WCD system 821, a general database 811, a patient-specific database 801, and a classification algorithm 850. Additional components may also be included; however, only those useful for this discussion are included in this example.

The general database 811 includes general patient data (referred to as "feature measurements") that have been collected from numerous patients and evaluated to determine if such patient data corresponds to a shockable event or a non-shockable event. In various embodiments, the patient data may include ECG readings from numerous patients who wore versions of the WCD system 821. The patient data, in this example, has been annotated to indicate whether each ECG reading constitutes a shockable ECG reading, a non-shockable ECG reading, or perhaps noise on the ECG signals. Alternative embodiments may also (or alternatively) include many other measured parameters, such as, by way of example only, SpO2, etCO2, respiration, heart sounds, or other signals or inputs. Values derived from these additional parameters also may be included in the algorithm. The general database 811 includes signals from a large number of people and adjudications (i.e. shock/no-shock classifications) from clinical experts such as physicians. In various embodiments, the general database 811 can be fixed or it could be updated periodically as new general patient data is acquired.

The classification algorithm 850 is an artificial intelligence (or machine learning) service that is configured to evaluate the patient data (e.g., feature measurements 812 from the general database 811) so as to construct coefficients for a Shock Index formula, such as that described above. As described above, the classification algorithm 850 uses machine learning techniques to evaluate measured patient data for determination of coefficients for the Shock Index formula that maximize the likelihood of an accurate shock/no-shock determination. The classification algorithm 850 is configured to perform such evaluation using general patient data, using patient specific data, or some combination of both general patient data and patient specific data.

The WCD system 821 of this embodiment includes a decision algorithm 822. The decision algorithm (e.g., Shock Advisory Algorithm of FIG. 2) may implement a Shock Index formula, as discussed above, to make a shock/no-shock determination. In certain embodiments, the Shock Index formula includes coefficients which each assign various weights to components of the Shock Index formula to better estimate whether a particular event being sensed is a shockable event.

In various embodiments, the WCD system 821 is pre-configured with coefficients for the Shock Index formula provided by the classification algorithm 850, such as when the WCD system 821 is first deployed. The WCD system 821 may also dynamically update the coefficients for the Shock Index Formula with new coefficients provided by the classification algorithm 850. In still other embodiments, the WCD system 821 may be configured to locally calculate and re-calculate coefficients as it either receives or measures new data.

The WCD system 821 is also configured to collect various patient-specific data, such as ECG measurements of the patient, environmental data (e.g., motion data) about the WCD system 821, and feedback provided by the patient (e.g., patient responses to alerts or other prompts). The WCD system 821 is still further configured to analyze, as discussed below, and transmit some or all of the patient specific data to a central repository of WCD related information. Such patient specific data may be stored in the patient specific database 801 accessible to the classification algorithm 850.

The patient specific database 801 includes patient data that is specific to a particular patient, and which has been annotated to discern whether the patient data (e.g., ECG segments) correspond to shockable events. One technique to help annotate the patient data is to include input received from the patient. For example, if a particular ECG segment for a patient suggests that a shock should be administered, a shock alarm may be raised prior to delivering the shock so that the patient can press a response button and cancel the shock. That patient feedback enables the WCD system 821 to identify that particular ECG segment as non-shockable. Thus, that particular ECG segment could be recorded in the patient specific database 801 and identified as a non-shockable segment. This technique can advantageously avoid a separate adjudication step because, in effect, the patient is serving as an adjudicator.

It should be noted that the nature of wearable medical devices, such as WCDs, makes embodiments of the instant disclosure particularly beneficial to such devices. For example, WCDs are typically prescribed to a specific patient and are worn for an extended period of time. As such, WCDs have an opportunity to learn from the prescribed patient and adapt over time. In contrast, an Automated External Defibrillator (AED) is most often used on patients that the AED has not encountered before and, therefore, the AED has had no opportunity to learn from those patients in advance of a cardiac arrest event. For at least that reason, the patient specific database 801 of the instant disclosure is advantageously used in conjunction with a wearable medical device.

Another way to identify a non-shockable segment is to see if the rhythm resolves itself without intervention. If no shock is given to a patient experiencing a questionable heart rhythm and the patient returns to a normal heart rhythm, then apparently, the patient did not need a shock. A large set of non-shockable segments can be collected in this way. This further technique can also advantageously avoid a separate additional adjudication step because, in effect, the WCD is serving as an adjudicator.

Over time, it is possible for the device to collect patient-specific segments known to be non-shockable. It is also possible to collect a set of shockable segments, but WCD shocks are not common so most patients wouldn't get many of those. Moreover, segment collection may emphasize high-rate rhythms, wide complexes, or other borderline conditions that are helpful to improve algorithm accuracy.

Still another way to categorize episodes is to use expert annotation or medical professionals to either annotate or to review episodes that have been stored. Annotations can be performed by the patient's personal physician using a review tool, or it could be an expert who is dedicated to reviewing episodes generated by the patient population. Such an expert might focus on annotating episodes for patient who are receiving a lot of false alarms, for example, or they might focus on new patients to ensure their algorithm gets trained properly. An expert also might review episodes that were automatically classified by methods described above.

Other embodiments may also use patient demographic information to aid in rhythm classification. The patient's age, sex, weight, body mass index, and other information may be considered as factors in the algorithm training. In addition, the patient's medical history may be considered. Important factors such as a prior history of VT/VF, or atrial fibrillation may help with algorithm discrimination. A complete medical history could include may factors PQRST measurements, baseline blood pressure, history of diabetes and other factors that may be assist algorithm discrimination.

Figure 9:
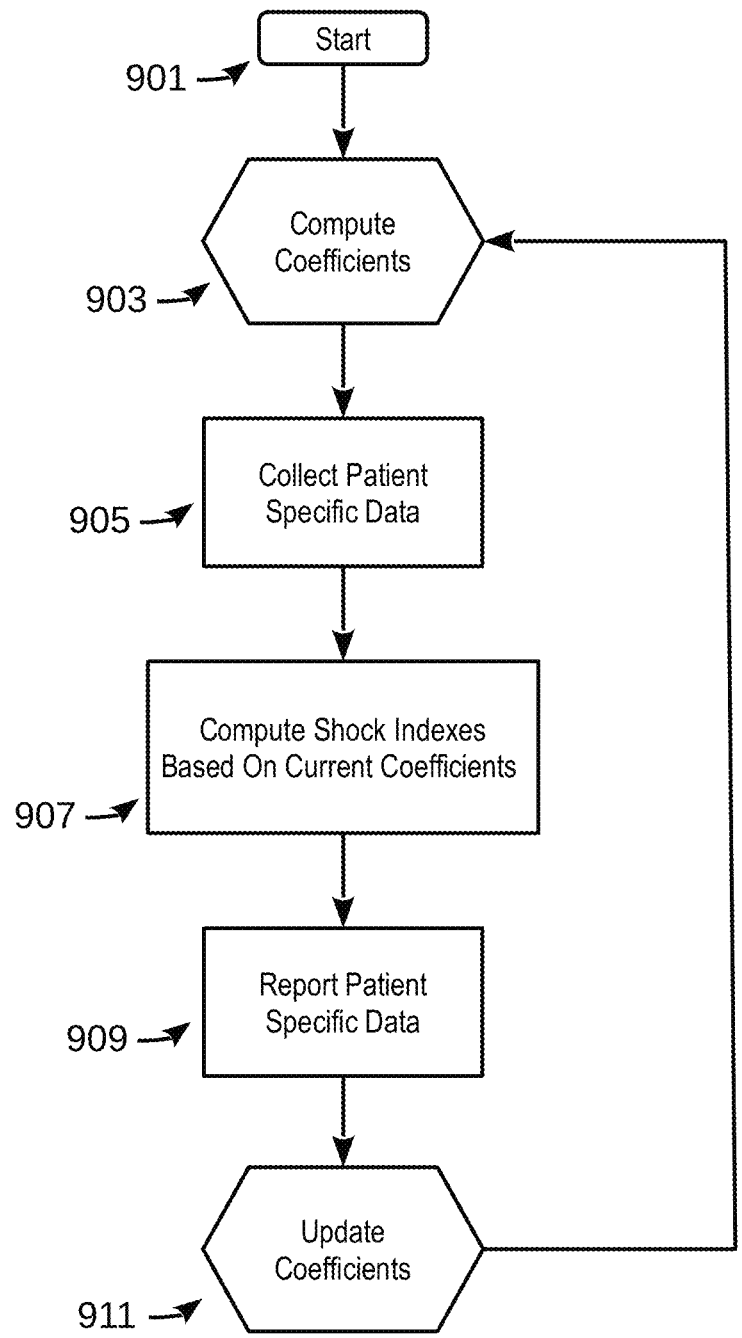
FIG. 9 is an operational flow diagram generally illustrating the operation of the WCD environment shown in FIG. 8.

FIG. 9 is an operational flow diagram generally illustrating the operation of WCD environment 800 shown in FIG. 8. In operation, at step 901, when a WCD system 821 is first worn, a patient may not have ECG history or a database of patient-specific data already available, so the Shock Index formula may be based on algorithm coefficients derived solely from the general database 811.

At step 903, a classification algorithm 850 computes coefficients based on the then-available patient parameter data. As noted, before any patient-specific data is available, the classification algorithm 850 may compute the coefficients based on general patient data from a general database 811.

At step 905, the WCD system 821 begins (or continues, as the case may be) collecting patient-specific data as the patient is wearing the WCD system 821. Collecting patient-specific data may be accomplished in any of the manners described above in conjunction with FIGS. 1-4. In particular, the patient-specific data may include ECG segments, analysis information for those ECG segments, patient responses to decisions based on those ECG segments, and the like.

At step 907, the WCD system 821 computes a Shock Index using (1) the Shock Index formula with the current coefficients and (2) the patient-specific data being collected by the WCD system 821 at step 905. As noted at length above, the WCD system 821 of the preferred embodiment includes a decision algorithm (e.g., Shock Advisory Algorithm of FIG. 2) that implements the Shock Index formula. By comparing the Shock Index to an index range (see, e.g., FIG. 5 and corresponding discussion), the WCD system 821 can make a shock/no-shock decision for each item of patient data (e.g., "patient parameters", FIG. 2 and corresponding discussion).

At step 909, the analyzed patient-specific data is reported. In various embodiments, reporting the patient-specific data may include transmitting the patient-specific data to a remote assistance center, or the like, for inclusion in a patient specific database 801. The patient-specific data may include all or some portion of the patient data collected at step 905. In addition, and preferably, the patient-specific data is transmitted together with results of the Shock Index analysis performed at step 907. Still further, the patient-specific data may further include additional information, such as patient responses and other environmental data, that corresponds with the patient-specific data.

At step 911, the coefficients for the Shock Index formula are updated in accordance with the patient-specific data and the process returns to step 903. In one embodiment, updating the coefficients is accomplished by returning the patient-specific data to the patient specific database 801 so that the classification algorithm can operate on both the general patient data and the patient-specific data together. In another embodiment, the patient-specific data may be stored locally at the WCD system 821 and an instance of the classification algorithm resident at the WCD system 821 may update the locally executing Shock Index formula with bespoke coefficients for the wearing patient. If enough patient-specific data is collected, that data could even replace data from in the general database. In that way, patients can learn that it is helpful to press the "response" button because the more they do, the better the algorithm learns their signal.

Returning to step 903, the classification algorithm 850 may again compute coefficients for the Shock Index formula using general patient data from the general database 811 and patient-specific data from the patient specific database 801. In certain embodiments, the patient-specific data may be given more weight than data in the general database 811. For instance, if the classification algorithm 850 is operative to compute coefficients on a patient-by-patient basis, tailored coefficients may be computed for each patient to which a WCD system is assigned.

Various Other Embodiments and Applications

As described at length above, embodiments of the disclosure may implement artificial intelligence methods, also referred to as machine learning, in shock/no shock decisions. In addition, such or similar methods can be also used in various other applications that will become apparent to those skilled in the art from a review of this disclosure. Two such applications include (1) training and/or managing of alerts and (2) Supraventricular Tachycardia discrimination, as will be described here.

Shock Alert Training and Management

A noise detection algorithm can be used to prevent noise from causing inappropriate shocks and unnecessary noise alerts. Machine learning can help identify noise and prevent noise from being misinterpreted by the algorithm. In one example, a two-step process comprises: (1) Identify and exclude noisy signals from analysis, and (2) Analyze non-noisy signals to make a shock/no-shock decision. In one example, an algorithm (either as described above or in any other manner) may be used in a shock/no-shock decision. However, in certain cases ECG signals used in that algorithm may be subject to noise, sometimes caused by poorly attached ECG leads or for other reasons. If the noise persists for an extended period of time (e.g., 5 minutes), the patient can be alerted to adjust their garment.

There are many techniques for detecting noise in an ECG signal. An algorithm may, for example, classify a signal as having noise if the peak-peak amplitude is greater than a Noise Threshold (e.g., 5 mV). Noise can also be detected by counting zero crossings or otherwise examining the frequency content of the signal. Noise metrics can be used individually or in conjunction to discriminate between a clean and a noisy signal. Noise metrics can also be combined with ECG measurements, such as R-R variability, QRS width variability, and QRS organization to improve accuracy. Differences in heart rate between channels may be indicative of noise. Having one or more leads off may also increase noise prevalence.

Accelerometer analysis can also be included in a noise detection technique. Accelerometer frequency, amplitude, duty cycle, and other measurements can be used in three axes to get a "signature" for specific patient activities. The signature for walking or running, or gait can be generated when the garment is fitted, and used for future reference. Put simply, a person walking or running is not in cardiac arrest.

In accordance with certain embodiments, heart rate "Agreement" is a score that is given to each channel (channel "x") based on whether other channels (channel "y") of a multichannel system show a similar heart rate. A channel with a high agreement score is most likely to have the correct heart rate.

Here is an example formula for a four (4) channel system:

$$\text{agreement } (x) = \left( \sum_{y=1}^{4} e^{-\frac{|(HR(x)-HR(y))|}{constant*HR(x)}} \right) - 1$$

A given channel receives an agreement score of 1 for every other channel that has the same heart rate. Channels that are similar but not identical may receive a partial score. In a four-channel system, agreement scores can range from zero to three.

For example, If the heart rates for four channels are 100, 120, 105, and 200, the agreement values, as computed using the formula above, are 0.74, 0.47, 0.86, 0.034 respectively.

Once a set of noise-related parameters are identified, machine learning can be used to find a "best" discrimination algorithm using a database of clean and noisy signals. For example, one noise detection algorithm can use the following pseudo-formula:

If peak-peak amplitude>5 mV, the signal is noisy
Otherwise,
NoiseIndex=A+B*Organization+C*Agreement+ D*Organization*Agreement+E*Organization^2+ F*Agreement^2
If NoiseIndex>a threshold, the signal is noisy
Otherwise, signal is not noisy.

Values for coefficients A, B, C, D, E, and F can be determined by machine learning based on a general database of signals. Example values of such coefficients may be:

A=115, B=−75, C=−56. D=19, E=9.9, F=6.9.

NoiseIndex values would be compared to a threshold to determine if a signal is noisy. An example threshold may be 25, for example. In this example, a signal with NoiseIndex>25 may be considered noisy.

This embodiment as derived from a large database of signals is one example that can be applied. In a further embodiment, the method may also be further tailored to an individual patient using the teachings as described above. The nature, pattern, or signature of a noise that one person generates may not be the same as another person, so fixed thresholds may not give the optimal performance.

In one embodiment, noise detection criteria can be tailored to a specific patient signal by collecting a set of clean and a set of noisy signals for a given patient, and using a machine learning technique to classify them. The dataset for classification can be signals collected from a single patient, or it can be combined with a dataset from a larger general database of patients, or both.

In various embodiments, and referring back to the discussion above, the general database may be annotated by experts to categorize signals as "Noisy" or "Non-noisy." The general database can include a wide range of ECG rhythms, including both shockable and non-shockable rhythms. In a preferred embodiment, Ventricular Fibrillation (VF) may also be included in the general database because clean VF can be difficult to distinguish from noise.

In addition, the patient-specific database may be classified as "Noisy" and "Non-noisy" based on various criteria, such as a combination of automatic measurements, patient inputs, and/or after-the-fact expert analysis. Non-noisy signals could be identified while the garment is being fitted, and/or during quiescent periods when the accelerometer indicates no movement, and/or when the NoiseIndex indicates a low noise value, such as 5 or less, etc. Noisy signals can be identified by a combination of (a) exceed a noise threshold and (b) inappropriately lead to a shock alarm. A shock alarm is known to be inappropriate if the patient presses the response button, or if no shock is given but the patient returns to a normal rhythm at a later time.

In specific embodiments, if a patient has common activities that generate ECG noise, the algorithm could be trained to avoid unnecessary alerts for those activities. For example, if alerts are generated while brushing teeth, mowing the lawn, or riding a motorcycle, then those signals can be recorded and identified as known activities that do not require an alert.

Supraventricular Tachycardia (SVT) Discrimination

In still other embodiments, AI methods can be used to discriminate SVT from VT. Traditional rhythm analysis algorithms may use a measurement, such as the QRS width, to distinguish VT (which requires a shock) from SVT (which should not be shocked). VT typically has wide QRS complexes, whereas SVT is typically narrow. A threshold of 120 mS is clinically used to distinguish between wide and narrow complexes.

A method of discriminating SVT from VT is to use a "template"—a snapshot of a normal ECG, also referred to as a baseline rhythm. If the morphology of a patient's measured ECG signal changes, it may be suspected of being VT. SVT typically has the same morphology as the baseline rhythm.

Traditionally SVT discriminators are applied in the VT Zone. The VT Zone may be defined as heart rates between 170-200 BPM, but lower or higher limits have been used as well.

Some patients have wide complexes all the time, so QRS width may distinguish VT for them. However, some patients have a morphology that changes with the heart rate, so a template may not work for those patients. Also, QRS morphology changes somewhat with posture, so a template-based discriminator needs to have limits that are loose enough to avoid tripping based on posture changes.

An improved method of SVT discrimination as disclosed herein is to use machine learning to better separate VT from SVT for a particular patient. In one embodiment, and again referring to the discussion above, the methods disclosed herein combine a set of known shockable segments from a general database with a set of known non-shockable segments for a particular patient. An ECG segment can be identified as non-shockable as discussed above, such as either because the patient pressed the response button or because no shock was delivered and the patient's rhythm eventually returned to normal on its own.

In another embodiment, an SVT discrimination method combines and processes parameters into an SVT Index, which can be similar to the shock index and/or the noise index discussed above. Factors include, but are not limited to QRS width, similarity to a stored template, R-R interval variability, and the rate of change of the heart rate at onset. Of course, other factors may also be included.

In one specific embodiment, the SVT discriminator could be applied only to rhythms that fall in the VT Zone. In another embodiment, the SVT discriminator could be applied over the entire range of heart rates. In an embodiment where the SVT discriminator is applied only to rhythms in the VT Zone, appropriate database and machine learning methods could be used when detected rates fall within the VT Zone. For example, shock decisions can then include decision points similar to the following:

Heart rates below VT threshold: No Shock
Heart rates above VF threshold: Shock
Heart rates in VT Zone: Shock if rhythm meets criteria defined by machine learning. No shock otherwise.

Still Other Applications of the Disclosed Technology

Although this disclosure has been written to describe embodiments that might be used by a WCD, other embodiments may be implemented in any long term monitor set up to detect specific conditions. For example, an MCOT device is worn by a patient for a period of time and automatically detects atrial fibrillation, atrial flutter, premature ventricular contractions (PVCs), and other aberrancies. Systems and methods that can be configured to monitor and/or treat health conditions can be trained using a general database combined with a patient-specific database to improve accuracy of detection.

Within a WCD, AI learning can be used to detect arrhythmias below the rate threshold and/or within a penumbra of thresholds to further raise recognition of changes and decision confidence. For example, if positive examples of high-rate atrial fibrillation have been identified and classified, then this information could be stored in a patient-specific database. That information could be helpful in identifying lower-rate atrial fibrillation that might otherwise be difficult to identify.

Other embodiments include combinations and sub-combinations of features described or shown in the drawings herein, including for example, embodiments that are equivalent to: providing or applying a feature in a different order than in a described embodiment, extracting an individual feature from one embodiment and inserting such feature into another embodiment; removing one or more features from an embodiment; or both removing one or more features from an embodiment and adding one or more features extracted from one or more other embodiments, while providing the advantages of the features incorporated in such combinations and sub-combinations. As used in this paragraph, feature or features can refer to the structures and/or functions of an apparatus, article of manufacture or system, and/or the steps, acts, or modalities of a method.

What is claimed is:

1. A patient-specific defibrillator system, comprising:
a support structure;
one or more sensors;
an energy storage device to store electrical charge;
one or more therapy electrodes; and
a processor coupled to the one or more sensors, the energy storage device, and the one or more therapy electrodes, wherein the processor is configured to:
use an algorithm to analyze information derived from signals output by the one or more sensors, the algorithm being used to determine a need for therapy by the patient-specific defibrillator system,
wherein the processor is further configured to dynamically calculate and re-calculate coefficients of the algorithm using an artificial intelligence analysis performed on data collected from multiple different persons, and
wherein the algorithm is derived, at least in part, from the artificial intelligence analysis performed on data collected from a patient using the one or more sensors; and based on the determination of the need for therapy by the patient-specific defibrillator system, cause at least some or all of the electrical charge stored in the energy storage device to be discharged through the one or more therapy electrodes while the support structure is being worn.

2. The patient-specific defibrillator system recited in claim 1, wherein the processor comprises a local processor, and wherein the local processor is further configured to communicate with a remote processor over a network.

3. The patient-specific defibrillator system recited in claim 2, wherein the algorithm is based, at least in part, on artificial intelligence processing, by the remote processor, of the data collected from the multiple different persons.

4. The patient-specific defibrillator system recited in claim 3, wherein the artificial intelligence processing comprises a logistic regression analysis.

5. The patient-specific defibrillator system recited in claim 4, wherein the processor is further configured to determine an index according to a formula: Index=$A*HR^2+B*HR+C*Width^2+D*Width+E$, where HR refers to Heart Rate, Width refers to a width of a QRS complex, and where the coefficients A, B, C, D, and E are determined using an artificial intelligence classification algorithm applied to the data collected from the multiple different persons.

6. The patient-specific defibrillator system recited in-claim 2, wherein the algorithm is updated with information derived from an artificial intelligence processing of the analyzed information, and wherein the updating comprises executing the artificial intelligence analysis on the local processor.

7. The patient-specific defibrillator system recited in claim 6, wherein the artificial intelligence processing comprises a logistic regression analysis.

8. The patient-specific defibrillator system recited in claim 2, wherein the local processor is further configured to transmit the analyzed information to the remote processor over the network.

9. The patient-specific defibrillator system recited in claim 8, wherein the local processor is further configured to receive, from the remote processor, the information derived from the artificial intelligence analysis of the analyzed information.

10. The patient-specific defibrillator system recited in claim 1, wherein the therapy comprises a shock delivered from the energy storage device through the one or more therapy electrodes.

11. The patient-specific defibrillator system recited in claim 1, wherein the processor is further configured to:
classify the analyzed information based on whether an action by the patient occurred,
based on the classification, update the algorithm with the information derived from the artificial intelligence analysis of the analyzed and classified information, and
use the updated algorithm to analyze subsequent information derived from the signals output by the one or more sensors while the patient-specific defibrillator system is being worn.

12. The patient-specific defibrillator system recited in claim 11, wherein the action by the patient comprises a response to an alert that a shock is about to be delivered.

13. The patient-specific defibrillator system recited in claim 12, wherein the response comprises an indication that the patient-specific defibrillator system should not deliver a shock from the energy storage device to the patient using the one or more therapy electrodes.

14. A wearable medical device, comprising:
one or more sensors; and
a processor coupled to the one or more sensors, wherein the processor is configured to:
  record patient-specific information derived from signals output by the one or more sensors while the wearable medical device is being worn by a patient,
  execute an algorithm to analyze the recorded patient-specific information, wherein the algorithm is based, at least in part, on data collected from multiple different persons,
  perform the artificial intelligence analysis of the recorded patient-specific information, wherein the artificial intelligence analysis is performed to dynamically calculate and re-calculate coefficients of the algorithm,
  update the algorithm with information derived from the artificial intelligence analysis of the recorded patient-specific information,
  use the updated algorithm to analyze subsequent information derived from the signals output by the one or more sensors while the wearable medical device is being worn, and
  cause an energy storage device to discharge a shock through a therapy electrode based, in part, on the algorithm indicating that the shock should be delivered.

15. The wearable medical device recited in claim 14, wherein the processor comprises a local processor, and wherein the local processor is further configured to communicate with a remote processor over a network.

16. The wearable medical device recited in claim 15, wherein the local processor is further configured to transmit the recorded patient-specific information to the remote processor, and wherein the remote processor is configured to perform the artificial intelligence analysis of the recorded patient-specific information.

17. The patient-specific defibrillator system recited in claim 1, wherein the processor is further configured to adjust the coefficients of the algorithm based on historical data, corresponding to the patient, collected from one or more previous instances of therapy administered to the patient.

18. The patient-specific defibrillator system recited in claim 1, wherein the processor is further configured to provide feedback to the patient via a visual or auditory interface, indicating current operational status of the patient-specific defibrillator system, including the need for therapy.

* * * * *